United States Patent [19]
Soderlund

[11] Patent Number: 5,248,524
[45] Date of Patent: Sep. 28, 1993

[54] METHOD AND APPARATUS FOR ZONED APPLICATION OF PARTICLES IN FIBROUS MATERIAL WITH DUAL DISPENSING NOZZLES

[75] Inventor: J. Donald Soderlund, Bellevue, Wash.

[73] Assignee: Paragon Trade Brands, Federal Way, Wash.

[21] Appl. No.: 825,930

[22] Filed: Jan. 27, 1992

[51] Int. Cl.$^5$ .............................................. B05D 1/14
[52] U.S. Cl. .................................... 427/200; 427/197; 427/202; 427/206; 118/308; 118/310; 118/314
[58] Field of Search ............... 427/180, 200, 206, 202, 427/197; 118/308, 310, 314; 239/551

[56] References Cited

U.S. PATENT DOCUMENTS

| | | | |
|---|---|---|---|
| 2,242,182 | 5/1941 | McCann | 118/308 |
| 2,577,205 | 12/1951 | Meyer et al. | 154/101 |
| 2,905,569 | 9/1959 | Zitke | 118/308 |
| 3,536,580 | 10/1970 | La Fave | 118/308 |
| 3,670,731 | 6/1972 | Harmon | 128/284 |
| 4,087,506 | 5/1978 | Cook et al. | 264/112 |
| 4,333,463 | 6/1982 | Holtman | 128/287 |
| 4,381,783 | 5/1983 | Elias | 604/368 |
| 4,543,274 | 9/1985 | Mulder | 427/197 |
| 4,551,191 | 11/1985 | Kock et al. | 156/276 |
| 4,600,603 | 7/1986 | Mulder | 118/308 |
| 4,685,915 | 8/1987 | Hasse et al. | 604/378 |
| 4,699,823 | 10/1987 | Kellenberger et al. | 428/219 |
| 4,770,344 | 9/1988 | Kaiser | 239/8 |
| 4,800,101 | 1/1990 | Takada | 427/197 |
| 4,924,803 | 5/1990 | Celant | 118/630 |
| 4,927,346 | 5/1990 | Kaiser et al. | 118/308 |
| 4,927,582 | 5/1990 | Bryson | 264/113 |
| 5,009,650 | 4/1991 | Bernardin | 604/378 |
| 5,017,324 | 5/1991 | Kaiser et al. | 264/510 |
| 5,028,224 | 7/1991 | Pieper et al. | 264/113 |

Primary Examiner—Shrive Beck
Assistant Examiner—Katherine A. Bareford
Attorney, Agent, or Firm—Dressler, Goldsmith, Shore, Sutker & Milnamow, Ltd.

[57] ABSTRACT

An apparatus and method for effecting zoned deposition of superabsorbent particles in a fibrous web includes the use of dual dispensing nozzles for forming selected deposition patterns. Fluidized streams of the superabsorbent particles are formed, with rotary valve assemblies employed for creating pulsed flow to each of the dispensing nozzles. The length, width, and relative positioning of the deposition patterns can be selectively varied in accordance with desired performance characteristics.

10 Claims, 4 Drawing Sheets

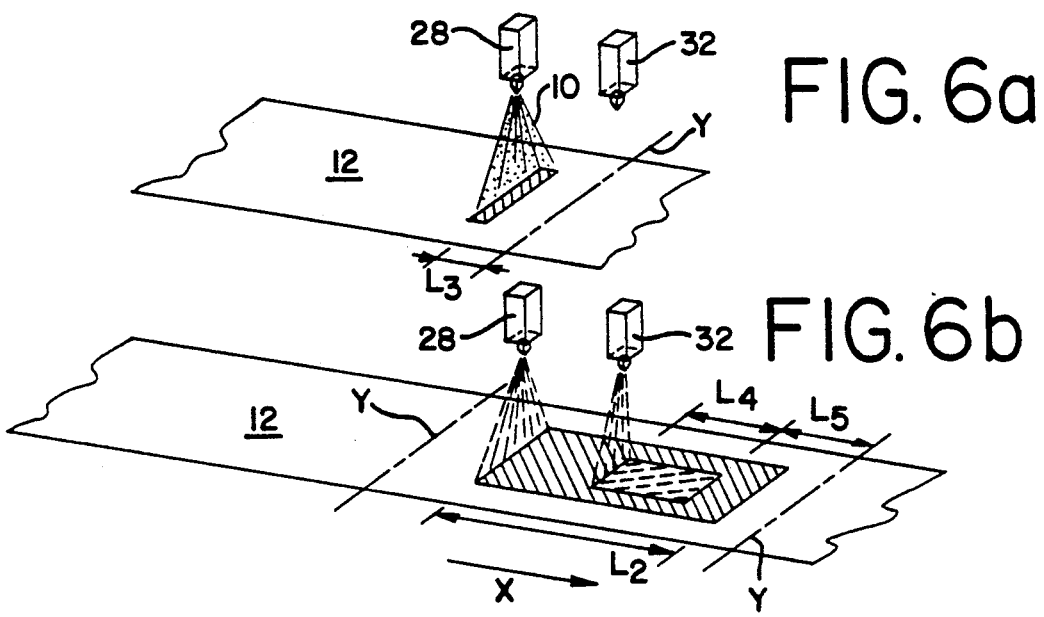
FIG. 6a
FIG. 6b
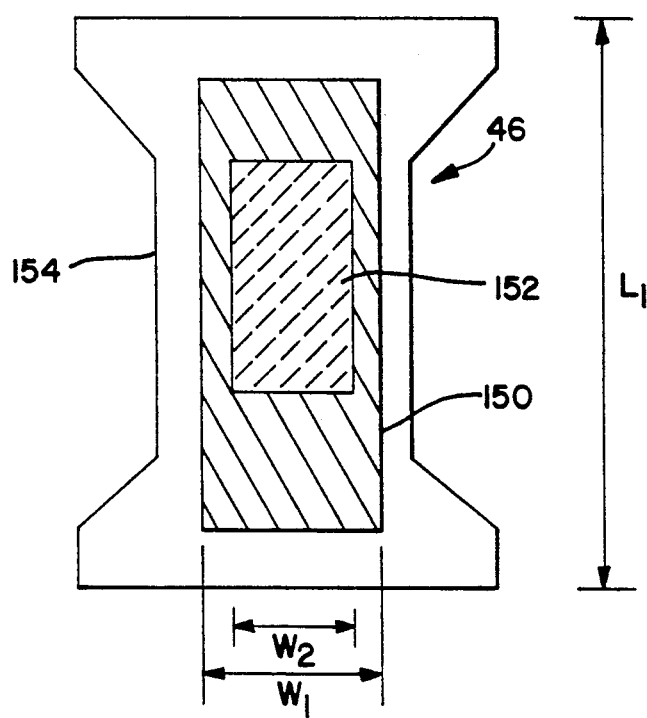
FIG. 7

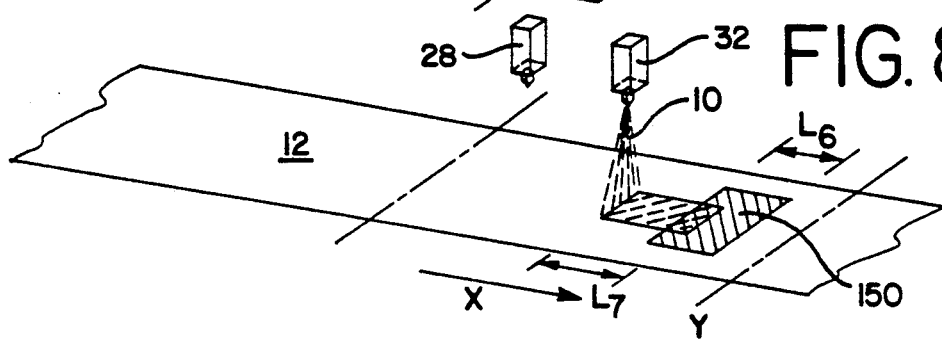
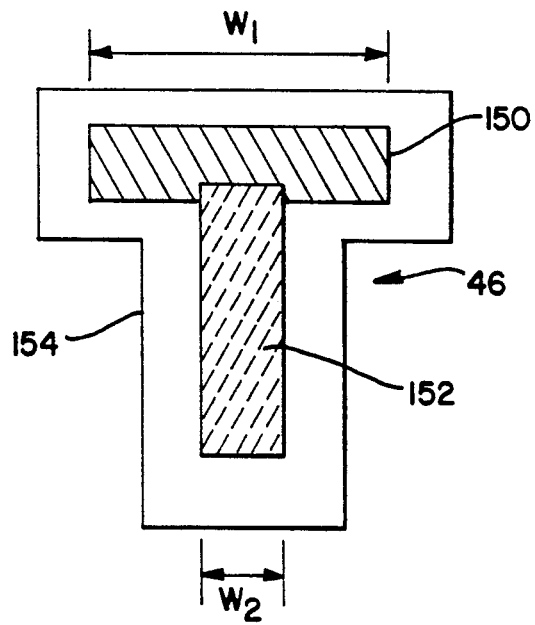

METHOD AND APPARATUS FOR ZONED APPLICATION OF PARTICLES IN FIBROUS MATERIAL WITH DUAL DISPENSING NOZZLES

TECHNICAL FIELD

The present invention relates generally to a method and apparatus for zoned application of particles in fibrous material, and more particularly to a method and apparatus for zoned application of superabsorbent polymer particles in an absorbent pad comprising hydrophilic fibrous material such as cellulose fibers, including the use of a pair of dispensing nozzles for pulsed deposition of superabsorbent particles.

BACKGROUND OF THE INVENTION

Disposable absorbent articles, such as disposable diapers and the like, usually have an absorbent panel containing superabsorbent polymers to increase the absorbent capacity of the panel while reducing the bulkiness of the article. For example, see U.S Pat. No. 3,670,731 to Harmon.

Particular absorbent panel constructions contain a zoned region of superabsorbent material in a selected portion of the panel in an attempt to make efficient use of the superabsorbent material. U.S. Pat. No. 4,333,463 to Holtman discloses an absorbent pad which contains a zoned region of superabsorbent material in its front upper or lower portion. U.S. Pat. No. 4,381,783 to Elais describes an absorbent article wherein one or more separate and distinct moisture-permeable cells or pockets containing superabsorbent particles are provided in a crotch region the article. U.S. Pat. No. 4,685,915 to Hasse et al. suggests application of a zoned deposit of superabsorbent polymers in a central portion of an absorbent article. U.S. Pat. No. 5,009,650 to Bernardin teaches an absorbent structure wherein superabsorbent material is located more at a rearward portion of an absorbent structure.

A number of methods and apparatus have been proposed to manufacture absorbent pad structures having a zoned deposit of superabsorbent material. U.S. Pat. No. 4,087,506 to Cook et al. discloses a method of polymer particles are applied onto a central zone of a moving web by means of a spreader. U.S. Pat. No. 4,551,191 to Kock et al. describes an arrangement wherein gas-entrained superabsorbent polymer particles are discharged through a nozzle having a predetermined width in a direction parallel to the direction of travel of the moving porous web so that they are uniformly deposited on the predetermined width portion of the web.

U.S. Pat. No. 4,800,102 to Takada discloses the use of a rotating screen disc having openings of various shapes at intervals, which disc is positioned between a superabsorbent supplier and a moving web so that superabsorbent polymer particles are intermittently deposited on the web at the intervals and patterns corresponding to the openings in the disc. U.S. Pat. Nos. 4,927,346 and 5,017,324 to Kaiser et al. respectively disclose an apparatus and a method for depositing superabsorbent polymer particles into a pad of fibrous material in a forming chamber. A controller selectively directs gas-entrained polymer particles either to a supply hopper or to the fibrous material to produce discrete patterns of superabsorbent polymers along the pad.

U.S. Pat. No. 4,927,582 to Bryson teaches another method for depositing superabsorbent particles into a pad in a forming chamber. The flow velocity of the superabsorbent polymer particles into the forming chamber is controlled so that a selected distribution of the polymer particles is achieved within the fibrous material deposited in the forming chamber. U.S. Pat. No. 5,028,224 to Pieper et al. teaches forming a split stream of superabsorbent material particles by centrifugal segregating means. The split stream is intermittently delivered into a forming chamber so that zoned regions of higher polymer density are formed within the fibrous material.

SUMMARY OF THE INVENTION

The present invention contemplates a method and apparatus for effecting selective zoned deposition of superabsorbent particles in a web of fibrous material, such as wood pulp fluff. By the present invention, highly efficient and controlled incorporation of said superabsorbent material in the fibrous material can be achieved for formation of individual absorbent panel assemblies, such as for disposable diapers or other absorbent products. Notably, the present invention contemplates that a pair of dispensing nozzle members are provided which are operatively connected with a supply of gas-entrained (i.e., air-entrained, or fluidized) superabsorbent particles via selectively operable valve means. By this arrangement, suitable operation of the valve means, in coordination with the conveyance of the fibrous material permits selective deposition of first and second discrete patterns of superabsorbent particles in the fibrous material.

In accordance with the illustrated embodiment, the present apparatus comprises a suitable conveyor for conveying the fibrous material for eventual formation of individual absorbent panel units. The conveying arrangement may take the form of a forming belt, operated in conjunction with a vacuum forming chamber, or may alternately be provided in the form of a rotary, drum-forming apparatus. Deposition of superabsorbent particles, in accordance with the present invention, can be effected either in conjunction with deposition of absorbent particles on the forming surface, or subsequent to deposition of such absorbent fibers.

In accordance with the illustrated embodiment, a pair of gas-entrained streams of superabsorbent particles is formed, with each stream respectively directed to a valve mechanism. In accordance with the preferred form, each valve comprises a rotary valve which acts to intermittently interrupt each gas stream, thereby providing pulsed flow of the superabsorbent particles.

Each of the rotary valves is respectively connected with first and second dispensing nozzle members. These nozzle members are positioned in operative association with the conveying arrangement to the fibrous web, with one nozzle preferably being arranged in alignment with, and downstream of, the other dispensing nozzle.

Selective and independent control of the rotary valves, in coordination with the movement of the fibrous web, permits highly versatile deposition of the superabsorbent particles in the fibrous material. Additionally, each of the dispensing nozzle members can be configured to provide a deposition pattern which differs in width from the other nozzle member. In this way, the superabsorbent particles can be deposited within the fibrous material in at least two different patterns having two different widths.

Other features and advantages of the present invention will become readily apparent from the following detailed description, the accompanying drawings, and the appended claims.

BRIEF DESCRIPTION OF THE DRAWINGS

FIGS. 6a and 6b are diagrammatic views illustrating formation of the patterns of superabsorbent particles in the associated fibrous web;

FIG. 7 is a diagrammatic view further illustrating patterns of superabsorbent particle deposition;

FIGS. 8a and 8b are diagrammatic views illustrating alternate patterns of deposition of superabsorbent particles; and FIG. 9 is a diagrammatic view illustrating alternate patterns of superabsorbent particle deposition in association with fibrous material.

DETAILED DESCRIPTION

Figure 1:
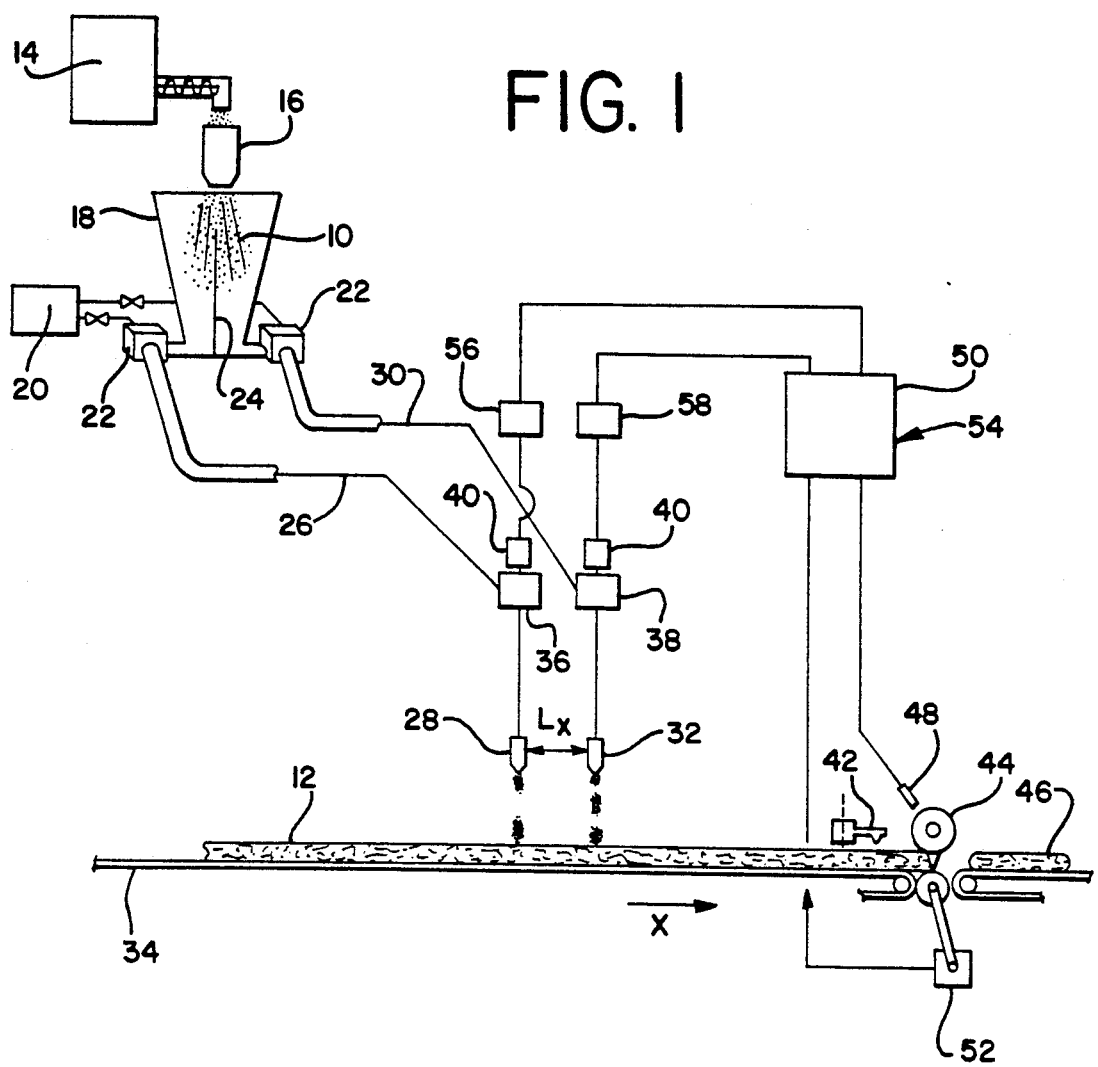
FIG. 1 is a diagrammatic view illustrating the method and apparatus of the present invention for effecting deposition of superabsorbent particles in a fibrous web.
Figure 2A:
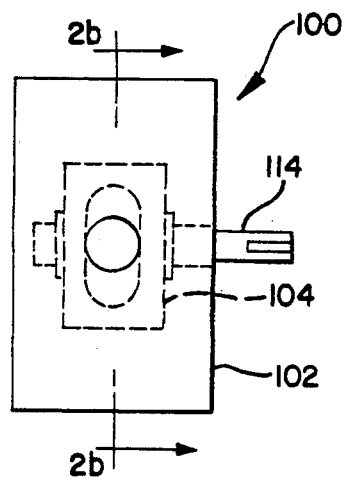
FIGS. 2a and 2b show a rotary valve of the present invention.
Figure 2B:
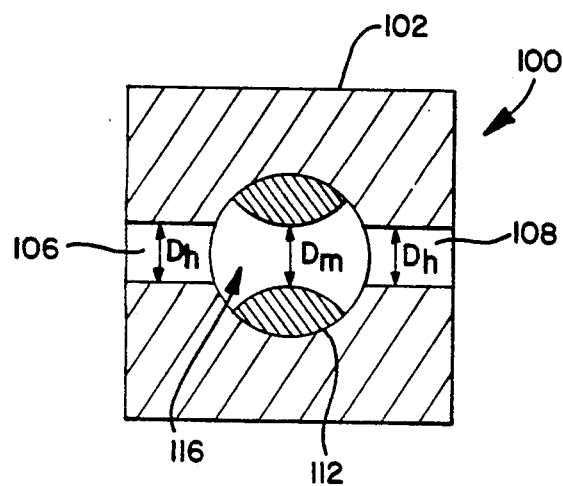
Figure 3A:
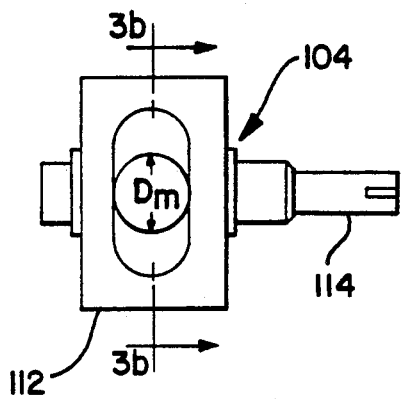
FIGS. 3a and 3b show, the valve rotor of the present rotary valve.
Figure 3B:
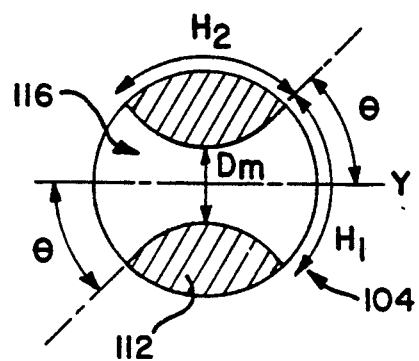
Figure 4A:
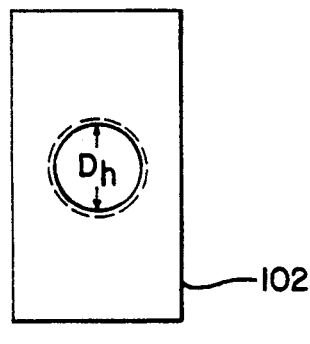
FIGS. 4a and 4b show the valve housing of the present rotary valve.
Figure 4B:
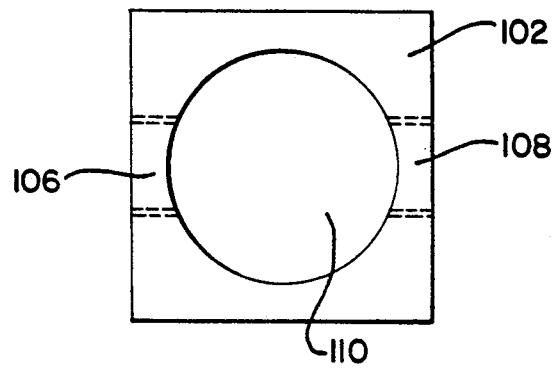

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

With reference now to FIG. 1, therein is illustrated an apparatus for zoned application of absorbent particles, such as superabsorbent polymer particles 10, in fibrous material 12, such as wood pulp fluff.

A delivery system provides a gas-entrained stream of absorbent particles 10. The delivery system generally comprises a auger feeder 14, a vibratory feeder 16, a funnel 18 and a compressed heated-gas supplier 20. The delivery system further includes a metering means (not shown) for metering and continuously delivering a predetermined amount of absorbent particles 10. The delivery system further includes a venturi means 22 to which a conduit means is connected to transfer the gas-entrained stream of absorbent particles. In the illustrated particular embodiment, funnel 18 is provided with a partition or flow divider 24 to preferably equally divide particle flow from the vibratory feeder 16.

Each divided particle flow portion is gas-entrained (typically air-entrained) at venturi means 22 to provide two fluidized streams of particles. A first conduit means 26 supplies the gas-entrained stream of one portion of the divided particle flow to a first nozzle member 28. A second conduit means 30 supplies the gas-entrained stream of another portion of the divided particle flow to a second nozzle member 32. First and second nozzle members 28, 32 are spaced from each other a predetermined distance $L_x$ in the moving direction X of the conveyer means 34 and respectively discharge absorbent particles 10 into fibrous material 12 being transported in a direction X by a conveyer means 34. Conveyor means 34 may comprise a forming belt or a rotary forming drum, with the nozzle members optionally being positioned to deposit superabsorbent particles either together with, or subsequent to, deposition on wood pulp fluff on the forming surface.

A first valve means 36 is connected between the first conduit means 26 and first nozzle member 28 to interrupt communication therebetween at a first time interval $T_1$. A second valve means 38 is connected between the second conduit means 30 and second nozzle member 32 to interrupt communication therebetween at a second time interval $T_2$. In a preferred embodiment, a rotary valve, driven by a servo-motor 40, is employed for each of first and second valve means 36, 38.

A continuous form of fibrous material 12 can be subjected to intermittent cut-outs at its respective opposite side edges by a water jet knife 42, and then separated by a rotary cutter 44 into an individual pad unit 46 having a length $L_1$, preferably after a zoned deposit of the absorbent particles applied therein. A knife proximity switch 48 generates and sends a knife reference signal to a servo-motion controller means 50. A line shaft encoder 52 generates and sends a line position signal to servo-motion controller means 50. Encoder may be adapted to generate 1000 pulses per revolution.

Servo-motion controller means 50 receives velocity profile information 54, in addition to the knife reference signals and line position signals, and send position commands respectively to a first servo drive means 56 and a second servo drive means 58 which respectively provide the associated servo-motor 40 with selected frequency. A servo-motor encoder (not shown), sends a servo-motor position signal back to servo drive means 56, 58.

FIGS. 2a through 4b shows a particular embodiment of a rotary valve 100 in accordance with the present invention for use as each valve means 36, 38. Rotary valve 100 includes a valve housing 102 and a rotor 104. Valve housing 102 has an inlet port 106 communicatively connected to the conduit means, an outlet port 108 communicatively connected to the nozzle member, and a valve opening 110 of cylindrical shape. Inlet port 106 and outlet port 108 have substantially the same diameter $D_h$. Rotor 104 includes a rotor member 112 and an axis shaft 114. Rotor member 112 is of a cylindrical configuration to be rotatably inserted in valve opening 110 of valve housing 102. Rotor member 112 is provided with a rotor opening 116, as best illustrated in FIGS. 3a and 3b, which has vertically enlarged configuration from a middle section toward opposite opening ends. The middle section is of circular shape and has the smallest diameter $D_m$ which is about equal to the diameter $D_h$ of the inlet and outlet ports of valve housing 102. Each opening end has a tapered maximum angle of $\theta$ relative to an opening axis Y. As shown in FIG. 3a, the opening shape is such that the circular shape of the middle section is gradually vertically elongated toward the opening end while maintaining a constant width thereof.

Each opening end of rotor member 112 has a circumferential arc length of $H_1$. An adjacent solid circumferential portion of rotor member 112 has a arc length of $H_2$. As appreciated from the foregoing description, in conjunction with the attached drawings, the open/close ratio of the rotary valve 110 is determined by the ratio $H_1/H_2$. Valve opening or closing time is controlled by a rotational speed of rotor member 112.

Figure 5:
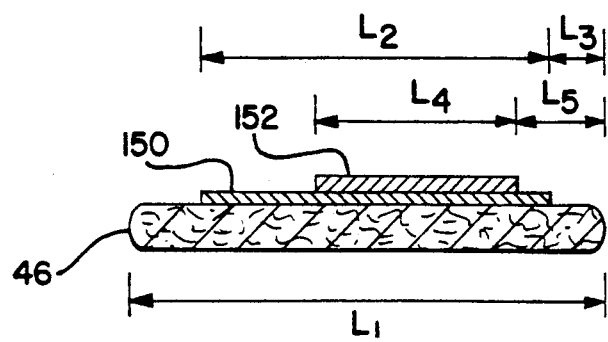
FIG. 5 is a diagrammatic view showing two patterns of deposition of superabsorbent particles in association with fibrous material.

For example, as shown in FIG. 5, servo-motion controller means 50, is responsive to the knife reference signals from proximity switch 48 and the line position signals from line shaft encoder 52. Based on the open-/close ratio $H_1/H_2$ of first rotary valve 36, the controller sends a first position command to first servo drive means 56. First servo drive means 56, responsive to the command and the servo-motor position signals from servo-motor encoder, causes rotor 104 to rotate to sequentially open and close communication between inlet port 106 and outlet port 108 in such a time-controlled manner that first nozzle member 28 places a first discrete deposit pattern 150 of absorbent particles having a length of $L_2$ in the continuous fibrous material 12, which pattern will have an offset length $L_3$ from a pad leading edge of individual pad unit 46 when cut by rotary cutter 44 at a later stage. Likewise, servo-motion controller means 50 send a second position command to second servo drive means 58 which causes rotor 104 to sequentially open and close communication between inlet port 106 and outlet port 108 in such a time-controlled manner that second nozzle member 32 places a second discrete deposit pattern 152 of absorbent particles having a length of $L_4$ on first deposit pattern 150, which will have an offset length $L_5$ from the pad leading edge of individual pad unit 46 when cut by rotary cutter 44 at the later stage of process.

Referring to FIGS. 6a and 6b, in conjunction with FIG. 7, another aspect of the present invention is illustrated. A continuous fluff pulp layer 12 is conveyed in the direction X at a predetermined speed. First and second nozzle members 28, 32 are positioned atop and along the moving direction X of continuous fluff pulp layer 12. Those nozzle members 28, 32 are substantially aligned along a lateral centerline of continuous fluff pulp layer 12 which substantially extends in the direction X, and are spaced from each other in that direction X. First and second nozzle members 28, 32 are configured to have different exit opening widths. In the illustrated particular embodiment, it is contemplated that first nozzle member 28 has a wider exit opening width than second nozzle member 32.

Referring to FIGS. 6a and 6b, in accordance with the process steps as described above with reference to FIG. 5, first nozzle member 28 is controlled to start discharging absorbent particles 10 as a cut line Y (along which fluff pulp layer 12 will be separated by rotary cutter 44 into individual pad units 46 each of length $L_1$ at the later process stage) passes first nozzle member 28 the distance $L_3$. First valve means 36 is controlled to close when first nozzle member 28 has discharged the gas-entrained absorbent particles 10 to provide in fluff pulp layer 12 first discrete deposit pattern 150 having the length $L_2$ and width $W_1$. First nozzle member 28 thus discharges absorbent particles 10 at a first interval to intermittently place first discrete deposit pattern 150 of absorbent particles 10 along the direction X in fluff pulp layer 12.

Second nozzle member 32 is controlled to start discharging absorbent particles 10 as the cut line Y passes second nozzle member 32 the distance $L_5$. Second valve means 38 is controlled to close when second nozzle member 32 has discharged the gas-entrained absorbent particles 10 to provide in fluff pulp layer 12 a second discrete deposit pattern 152 having the length $L_4$ and a width $W_2$. Second nozzle member 32 thus discharges absorbent particles 10 at a second interval to intermittently place second discrete deposit pattern 152 of absorbent particles 10 along the direction X in fluff pulp layer 12.

The fluff pulp layer portion with such zoned deposit of absorbent particles 10 is then at its respective opposite side edges intermittently cut out by water jet knife 42 to form leg holes 154, and is finally separated into the individual pad unit 46 customized for disposable diaper use. As illustrated in FIG. 7 wherein second discrete deposit pattern 152 of absorbent particles is placed toward the leading edge of the individual absorbent pad unit 46 and toward a lateral centerline of the individual absorbent pad unit 46 to create an overlapped region, which corresponds to second discrete deposit pattern 152, in a front middle region of the individual absorbent pad unit 46 to thereby increase a density of absorbent particles, that is, an absorbent capacity in a front middle region of the individual absorbent pad unit 46.

While first nozzle member 28 is described to have the wider exit opening than the second nozzle member 32 in the above embodiment, such widths $W_1$ and $W_2$ may be reversed between the two nozzle members. In such instance, in accordance with the desired distances $L_3$ and $L_5$ from a leading edge of individual pad unit 46, and the distance between first and second nozzle members 28, 32, the servo-motion controller means 50 will be set to send control commands so that either of first and second nozzle members 28, 32 initiates discharging the gas-entrained absorbent particles 10 in fluff pulp layer 12 to provide the zoned pattern of absorbent particles as shown in FIG. 7.

As appreciated from the foregoing description, the selected differentiation of nozzle exit opening widths between first and second nozzle members 28, 32 allows individual absorbent pad unit 46 to form a desired stepwise change in a transverse or (cross-direction) density profile of absorbent particles 10.

Now referring to FIGS. 8a and 8b, in conjunction with FIG. 9, still another aspect of the present invention is illustrated. Process steps are substantially the same except that the first and second time intervals are differently set, for example, by changing the rotational speeds of first and second rotary valves 36, 38. First valve means 36 is controlled to discharge the gas-entrained absorbent particles 10 at a differently-set first interval to provide in fluff pulp layer 12 first discrete deposit pattern 150 having a length $L_6$ and the width $W_1$. Second valve means 38 is controlled to discharge the gas-entrained absorbent particles 10 at a differently-set second interval to provide in fluff pulp layer 12 second discrete deposit pattern 152 having a length $L_7$ and the width $W_2$. The fluff pulp layer portion with such T-shaped zoned deposit of absorbent particles 10 is then at its respective opposite side edges intermittently cut out by water jet knife 42 to form leg holes 154, and is finally separated into individual pad unit 46 of T-shape, as illustrated in FIG. 9.

As will be clearly understood from the foregoing description, an I-shaped zoned deposit of absorbent particles 10 may be applied by changing the first interval, for example, by accordingly decreasing the length ratio $H_1/H_2$ of first rotary valve 36. Similarly, a desired selection of the overlapped region may also be available by changing the first and/or second pulse intervals.

As appreciated from the above-exemplified embodiment, a selected set of the interval settings, exit opening widths of the nozzle members, and positioning of the nozzle members allows the zoned deposit of absorbent particles to be desirably shaped in the fibrous material. Additionally, the system can be operated such that one or both of the particle dispensing nozzles dispense plural zones of absorbent particles within the length of an individual absorbent panel unit.

Absorbent particles 10 may be any type of absorbent material in a particle form. Suitable absorbent material includes absorbent fibers, superabsorbent polymers, absorbent fiber/polymer composites, or any equivalent or combination thereof.

Fibrous material 12 preferably comprises cellulosic fibers such as wood pulp fibers, cotton linters, and the like. Other cellulosic fibers that might be used are rayon fibers, flax, jute and the like. Alternatively, hydrophilized synthetic fibers may be used. Such synthetic fibers include polyethylene, polypropylene, nylon, polyester and the like.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover by the appended claims all such modifications as fall within the scope of the claims.

What is claimed is:

1. A process for zoned application of superabsorbent particles in fibrous material comprising the steps of:
    moving said fibrous material in one direction;
    supplying a continuous gas-entrained stream of said superabsorbent particles through conduit means;
    providing first and second nozzle members connected to said conduit means for discharging said gas-entrained superabsorbent particles into said fibrous material;
    spacing said first and second nozzle members from each other in at least one direction,
    providing first valve means connected between said conduit means and said first nozzle member for interrupting communication between said conduit means and said first nozzle member at a first interval so that said first nozzle member discharges a pulsed stream of said superabsorbent particles to provide a first deposit pattern of said superabsorbent particles having a first width in said fibrous material;
    providing second valve means connected between said conduit means and said second nozzle member for interrupting communication between said conduit means and said second nozzle member at a second interval so that said second nozzle member discharges a pulsed stream of said superabsorbent particles to provide a second deposit pattern of said superabsorbent particles having a second width different from said first width in said fibrous material; and
    selecting said first and second intervals to provide a desired combination of said first and second deposit patterns of said particles in an overlapped manner which includes a step-wise change in a cross-direction density profile of said superabsorbent particles in said fibrous material.

2. The process of claim 1, wherein
    said first and second nozzle members have different exit opening widths so as to provide said stepwise change in a cross-direction density profile of said superabsorbent particles in said fibrous material along said one direction.

3. The process of claim 1, wherein
    said first and second nozzle members are aligned with each other along said one direction so that either of first and second deposit patterns of the superabsorbent particles is encompassed in the other deposit pattern of the superabsorbent particles in an overlapped region thereof.

4. The process of claim 1, wherein
    said first and second deposit patterns are combined to provide a discrete deposit zone of said superabsorbent particles which has a desired shape.

5. The process of claim 4, wherein
    said discrete deposit zone of the superabsorbent particles is T-shaped.

6. The process of claim 1, wherein
    said valve means is a diverter valve.

7. The process of claim 1, wherein
    said valve means is a rotary valve.

8. An apparatus for zoned application of superabsorbent particles in fibrous material comprising the steps of:
    moving said fibrous material in one direction:
    supplying a continuous gas-entrained stream of said superabsorbent particles through conduit means;
    providing first and second nozzle members connected to said conduit means for discharging said gas-entrained superabsorbent particles into said fibrous material;
    spacing said first and second nozzle members from each other so as to be positioned in alignment with each other along said one direction;
    providing first valve means connected between said conduit means and said first nozzle member for interrupting communication between said conduit means and said first nozzle member at a first interval so that said first nozzle member discharges a pulsed stream of said superabsorbent particles to provide a first deposit pattern of said superabsorbent particles having first length and width in said fibrous material;
    providing second valve means connected between said conduit means and said second nozzle member for interrupting communication between said conduit means and said second nozzle member at a second interval so that said second nozzle member discharges a pulsed stream of said superabsorbent particles to provide a second deposit pattern of said superabsorbent particles having second length and width in said fibrous web, wherein said second width is different from said first width;
    selecting said first and second intervals to provide in said fibrous web a desired combination of said first and second deposit patterns of said particles which includes an overlapped region for increased absorbent capacity, said region having a length equal to or smaller than one of said first and second lengths, and having a width equal to the smaller one of said first and second widths.

9. The process of claim 8, wherein
    said first deposit pattern in configured to encompass said second deposit pattern so that said second deposit pattern corresponds to said overlapped region.

10. The process of claim 9, wherein
    aid overlapped region is provided toward a leading edge of an individual absorbent pad unit intended to be separated as an end product.

* * * * *

UNITED STATES PATENT AND TRADEMARK OFFICE
CERTIFICATE OF CORRECTION

PATENT NO. : 5,248,524
DATED : September 28, 1993
INVENTOR(S) : J. Donald Soderlund It is certified that error appears in the above-indentified patent and that said Letters Patent is hereby corrected as shown below:

In column 1, line 43, after "of", insert --producing a fluid absorbent web wherein superabsorbent--;

In column 8, line 19, "An apparatus" should be --A process--.

Signed and Sealed this

Twelfth Day of April, 1994

Attest:

BRUCE LEHMAN

Attesting Officer    Commissioner of Patents and Trademarks